(12) United States Patent
Karseboom et al.

(10) Patent No.: US 6,455,739 B1
(45) Date of Patent: Sep. 24, 2002

(54) PRODUCTION OF 4-FLUOROBENZALDEHYDE

(75) Inventors: Steven G. Karseboom; Michael J. Turpie, both of Baton Rouge; Phillip R. Devrou, Denham Springs; John F. Balhoff, Baton Rouge, all of LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/949,380

(22) Filed: Sep. 7, 2001

(51) Int. Cl.[7] .............................................. C07C 45/50
(52) U.S. Cl. ..................... 568/437; 568/428; 568/809
(58) Field of Search ................................. 568/428, 437, 568/809

(56) References Cited

U.S. PATENT DOCUMENTS

| | | | |
|---|---|---|---|
| 1,939,005 A | 12/1933 | Guthke | 260/136 |
| 4,420,433 A | 12/1983 | Braden et al. | 260/544 D |
| 4,446,075 A | 5/1984 | Eiglmeier et al. | 260/465 G |
| 4,585,898 A | 4/1986 | Lau et al. | 568/433 |
| 4,585,899 A | 4/1986 | Gelbein et al. | 568/435 |
| 4,585,900 A | 4/1986 | Holy et al. | 568/435 |
| 4,588,844 A | 5/1986 | Kysela et al. | 568/41 |
| 4,605,749 A | 8/1986 | Buchman et al. | 549/70 |
| 4,622,429 A | 11/1986 | Blank et al. | 568/428 |
| 4,885,412 A | 12/1989 | Pennington et al. | 568/469.9 |
| 5,068,450 A | 11/1991 | Crochemore et al. | 568/435 |
| 5,138,099 A | 8/1992 | Lang | 568/435 |
| 5,347,054 A | 9/1994 | Billeb et al. | 568/437 |
| 5,382,694 A | 1/1995 | Billeb et al. | 568/437 |
| 5,585,523 A | 12/1996 | Weiguny et al. | 568/435 |
| 5,648,551 A | 7/1997 | Borchert et al. | 568/431 |
| 6,300,525 B1 * | 10/2001 | Anderson et al. | 568/428 |

FOREIGN PATENT DOCUMENTS

| | | |
|---|---|---|
| DE | 281212 | 12/1914 |
| DE | 403489 | 9/1924 |
| DE | 529809 | 7/1931 |
| GB | 3152 | 2/1916 |

OTHER PUBLICATIONS

Caplus Abstract of, Xie et al. "Synthesis of P–Fluorobenzaldehyde", Huagong Shikon, 1998, 12(6), pp. 30–31.

Noskov et al., "Palladium–Catalyzed Carbonylation of Chlorobenzene in the Presence of Lewis Acids", React. Kinet. Catal. Lett., vol. 64, No. 2, 1998, pp. 359–363.

Okano et al., "Formylation of Aryl Halides with Carbon Monoxide and Sodium Formate in the Presence of Palladium Catalyst", Bull. Chem. Soc. Jpn., 1994, vol. 67, pp. 2329–2332.

Tanaka et al., "formylation of Aromatic Compounds with CO in $HSO_3F$–$SbF_5$ under Atmospheric Pressure", J. Org. Chem., 1992, 57, pp. 2677–2680.

Toniolo et al., "metals in Organic Synthesis", V. The Gattermann–koch Synthesis of Aromatic Aldehydes Promoted by $CuCl(PPh_3)_n$ (n=0,1 or3). Is the Cuprous Complex necessary in the Synthesis of Tolualdehyde? Journal of Organometallic Chemistry, vol. 194, 1980, pp. 221–228.

* cited by examiner

Primary Examiner—Sreeni Padmanabhan
(74) Attorney, Agent, or Firm—Philip M. Pippenger (57) ABSTRACT

4-Fluorobenzaldehyde is produced by a commercially feasible process. The process comprises heating a mixture of fluorobenzene and a strong Lewis acid with dissolved hydrogen halide in an atmosphere of carbon monoxide at about 45 to about 100° C. and at a total pressure of about 150 psig up to the maximum pressure rating of the reactor. Formed is a reaction mass containing a Lewis acid complex of 4-fluorobenzaldehyde and at least a halobis(fluorophenyl) methane by-product. The complex is broken by quenching the reaction mass with a Lewis acid-solvating liquid to liberate 4-fluorobenzaldehyde. By-product halobis (fluorophenyl)methane is converted to di(fluorophenyl) methanol to avoid potential corrosion problems and formation of light sensitive color bodies in the recovered 4-fluorobenzaldehyde.

43 Claims, 6 Drawing Sheets

PRODUCTION OF 4-FLUOROBENZALDEHYDE

TECHNICAL FIELD

This invention relates to process technology suitable for producing on an industrial scale 4-fluorobenzaldehyde, a useful raw material for producing certain pharmaceutical products.

BACKGROUND

Over the years a number of laboratory synthesis procedures have been published in the technical and patent literature for preparation of various aromatic aldehydes from benzene or substituted benzenes using carbon monoxide and a Lewis acid such as aluminum chloride. While some of these procedures can be conducted on a laboratory scale, they are often unsuitable for use on an industrial scale for various reasons such as low yields or use of impractical or uneconomical reaction conditions. Moreover, such laboratory procedures usually fail to take into consideration problems which can arise because of by-products which often are formed in the course of the methods used.

An objective of this invention is to provide process technology suitable for producing 4-fluorobenzaldehyde on an industrial scale.

SUMMARY OF THE INVENTION

This invention provides process technology which is suitable for producing 4-fluorobenzaldehyde on a commercial scale. The process technology of this invention not only makes possible the production of 4-fluorobenzaldehyde in good yields under practical reaction conditions, but in addition avoids or at least minimizes potential corrosion problems that could otherwise occur in actual practice in industrial plant facilities due to the formation of relatively small amounts of halobis(fluorophenyl)methane as a by-product of the reaction. In addition, this invention eliminates or at least minimizes the extent to which the final reaction product discolors on exposure to light.

Pursuant to one embodiment of this invention, 4-fluorobenzaldehyde is produced by a process which comprises:

A) heating in a reactor a mixture of fluorobenzene and a strong Lewis acid, most preferably aluminum chloride, in the presence of a hydrogen halide and in a carbon monoxide atmosphere at a temperature in the range of about 45 to about 100° C. and at a total pressure in the range of about 150 psig to the maximum pressure rating of the reactor being used to form a reaction mass comprising at least (i) a complex of 4-fluorobenzaldehyde with the Lewis acid used, and (ii) halobis(fluorophenyl)methane by-product;

B) breaking such complex by quenching the reaction mass with a Lewis acid-solvating liquid such as water to liberate 4-fluorobenzaldehyde; and C) converting halobis(fluorophenyl)methane into di(fluorophenyl)methanol, to thereby eliminate or reduce potential corrosion problems and development of color in the 4-fluorobenzaldehyde on exposure to light.

Accordingly, the process makes it possible to either (i) recover 4-fluorobenzaldehyde or (ii) use the 4-fluorobenzaldehyde as a reactant without isolation without encountering significant corrosion or color formation in the product.

Of the hydrogen halides that can be used in the above process (HCl, HBr, HI, and/or HF), HCl and/or HBr are preferred, with HCl being most preferred. Such hydrogen halides should be anhydrous or essentially anhydrous, i.e., the amount of water, if any, present therein should be so small as to have no material effect upon the reaction. When the hydrogen halide and/or the Lewis acid contains chlorine, chlorobis(fluorophenyl)methane is formed as a by-product in the reaction. Similarly, when the hydrogen halide and/or the Lewis acid contains bromine, bromobis(fluorophenyl) methane is formed as a by-product in the reaction. Mixtures of chlorobis(fluorophenyl)methane and bromobis (fluorophenyl)methane are formed as by-products when the hydrogen halide and/or the Lewis acid provide both chlorine and bromine to the reaction mixture.

In selecting the Lewis acid for use in the process, consideration should be given to the materials of construction of the facilities used in the process. For example, with plant facilities fabricated from Hastelloy B, it is desirable to avoid use of a Lewis acid in the form of a metal halide having at least two different valence states, such as ferric chloride and ferrous chloride as excessive corrosion may be encountered.

Use of HCl and a Lewis acid chloride salt is preferred from a cost-effectiveness and performance standpoint subject to the above corrosion considerations relative to metal chlorides having different valence states.

By converting the halobis(fluorophenyl)methane into di(fluorophenyl)methanol, corrosion problems that would otherwise occur in many plant facilities during subsequent recovery operations are avoided or at least significantly minimized. Such recovery operations typically involve one or more vessels, distillation columns, or exchangers fabricated from metals such as carbon steel and/or stainless steel. These metals are susceptible to attack by aqueous acids. Because trace amounts of water in the organic phase or residual water in reactors can react with the halobis (fluorophenyl)methane to release hydrogen halide such as HCl or HBr, recovery operations performed in recovery equipment fabricated from carbon steel or stainless steel would be subject to excessive corrosion. Therefore, in the conduct of the above process, this potential problem is avoided or at least greatly minimized by converting the halobis(fluorophenyl)methane into di(fluorophenyl) methanol.

Preferably, 4-fluorobenzaldehyde is recovered from the reaction mass after conducting step C) above. However, in some cases the 4-fluorobenzaldehyde can be used as a reactant while present in the reaction mass after conducting step C). For example, the reaction mass from step C) could be catalytically hydrogenated in order to convert the 4-fluorobenzaldehyde to 4-fluorobenzyl alcohol.

A preferred embodiment of this invention is a process which comprises:

a) heating in a reactor a mixture of fluorobenzene and aluminum chloride with dissolved anhydrous or essentially anhydrous HCl and in an atmosphere of carbon monoxide at a temperature in the range of about 45 to about 100° C. and at a total pressure of at least about 150 psig but no higher than the maximum pressure rating of the reactor, to form a reaction mass containing an aluminum chloride complex of 4-fluorobenzaldehyde and at least chlorobis(fluorophenyl)methane by-product;

b) breaking the aluminum chloride complex by quenching the reaction mass with an aluminum chloride-solvating liquid, such as water, to liberate 4-fluorobenzaldehyde;

c) converting chlorobis(fluorophenyl)methane into di(fluorophenyl)methanol; and d) either (i) recovering 4-fluorobenzaldehyde from the resultant reaction mass, or (ii) using the 4-fluorobenzaldehyde as a reactant without isolation.

In conducting d) of this process it is preferable to recover the 4-fluorobenzaldehyde from the resultant reaction mass.

One procedure which can be effectively utilized in conducting the above preferred embodiment involves the following:

in the conduct of b), a two-phase liquid mixture is formed composed of an aqueous phase and an organic phase comprised of 4-fluorobenzaldehyde together with unreacted fluorobenzene and by-products which include at least chlorobis(fluorophenyl)methane, 2-fluorobenzaldehyde, and 3-fluorobenzaldehyde, said two-phase liquid mixture optionally containing solids comprising hydrated aluminum chloride, and wherein the 4-fluorobenzaldehyde is recovered by separating the phases formed in the conduct of b);

in the conduct of c) chlorobis(fluorophenyl)methane by-product in the separated organic phase is hydrolyzed to di(fluorophenyl)methanol;

in the conduct of d), components that boil at lower temperatures than 4-fluorobenzaldehyde are distilled from the resultant organic phase, and 4-fluorobenzaldehyde is separated by distillation from the less volatile components remaining in the organic phase, said less volatile components comprising at least di(fluorophenyl)methanol.

In a particularly preferred embodiment of this invention, 4-fluorobenzaldehyde is produced by a process which comprises:

a) heating a mixture of fluorobenzene and aluminum chloride in the presence of dissolved anhydrous or essentially anhydrous HCl in an atmosphere of carbon monoxide at a temperature in the range of about 45 to about 90° C. and at a total pressure in the range of about 250 psig up to the maximum pressure rating of the reactor being used to form a reaction mass comprising an aluminum chloride complex of 4-fluorobenzaldehyde and chlorobis (fluorophenyl)methane by-product;

b) quenching the reaction mass with water or a dilute aqueous acid such as hydrochloric acid to liberate 4-fluorobenzaldehyde from the aluminum chloride complex and form an organic phase and an aqueous phase free of precipitated aluminum salts;

c) separating the organic phase from the aqueous phase;

d) converting chlorobis(fluorophenyl)methane in the organic phase into di(fluorophenyl)methanol; and e) optionally, but preferably, recovering 4-fluorobenzaldehyde from the organic phase.

The organic phase formed in b) above will usually comprise 4-fluorobenzaldehyde together with some unreacted fluorobenzene and by-products which include at least chlorobis (fluorophenyl)methane and typically small amounts of 2-fluorobenzaldehyde, 3-fluorobenzaldehyde, and oligomeric materials. The chlorobis(fluorophenyl)methane by-product in this organic phase mixture is hydrolyzed to di(fluorophenyl)methanol, preferably by alkaline hydrolysis, for two main reasons: (1) to minimize corrosion of workup apparatus by HCl that otherwise would have been formed from the hydrolysis of chlorobis(fluorophenyl) methane during an ensuing stripping operation, and (2) to avoid formation of color bodies in the final product.

The magnitude of potential corrosion problem is illustrated by the fact that if the fluorobenzene strip/distillation is conducted without hydrolyzing the chlorobis(fluorophenyl) methane, corrosion rates in excess of 25 mils per year can be experienced with 316L stainless steel in the overhead system. Carbon steel would be expected to have a corrosion rate of at least that magnitude. In contrast, available experimental data indicates that by converting the chlorobis (fluorophenyl)methane to di(fluorophenyl)methanol, the corresponding corrosion rate of the above overhead system should be no more than about 1 mil per year.

In conducting e) above it is preferred to flash or distill from the organic phase components that boil at lower temperatures than 4-fluorobenzaldehyde, including the structural isomers of 4-fluorobenzaldehyde, and to then separate the 4-fluorobenzaldehyde by distillation from the less volatile components in the remaining organic phase such as the di(fluorophenyl)methanol. Alternatively, the 4-fluorobenzaldehyde can be separated as a sidestream during the distillation. To minimize the possibility of emulsion formation during the hydrolysis of the CBFPM in d), it is particularly preferred to wash the separated organic phase from c) with dilute aqueous acid to remove residual aluminum chloride, again separate the phases, and then hydrolyze the chlorobis(fluorophenyl)methane by-product in this separated organic phase to di(fluorophenyl)methanol, followed by distilling from the organic phase components that boil at lower temperatures than 4-fluorobenzaldehyde, and to separate from the remaining organic phase the 4-fluorobenzaldehyde from the less volatile components such as di(fluorophenyl)methanol.

Other embodiments, features and advantages of this invention will become still further apparent from the ensuing description, accompanying drawings, and appended claims.

FURTHER DETAILED DESCRIPTION

Carbonylation Reaction

As can be seen from the above, a principal chemical reaction involved in the practice of this invention is, in essence, a catalyzed regioselective carbonylation reaction using carbon monoxide. In conducting this reaction, hydrogen halide is used as the catalyst and the Lewis acid is used in at least an equimolar quantity relative to the fluorobenzene as a reactant to form a Lewis acid complex of 4-fluorobenzaldehyde. The reaction is performed using an atmosphere of carbon monoxide with or without the inclusion of an inert gas such as nitrogen or argon, which can be co-fed with the carbon monoxide or which can be precharged to the reactor prior to the introduction of the carbon monoxide. Typically, the vapor space in the reactor will contain some gaseous hydrogen halide in equilibrium with dissolved hydrogen halide present in the liquid phase. The carbonylation reaction is usually conducted at a temperature in the range of about 45 to about 100° C., and preferably in the range of about 45 to about 90° C., and at a pressure in the range of about 150 psig up to the pressure rating of the reactor being used, and preferably in the range of about 250 psig up to the pressure rating of the reactor being used. In cases where high pressure autoclaves are not available, very good results can be achieved at temperatures in the range of about 60 to about 70° C. with total pressures in the range of about 150 to about 500 psig, and especially in the range of about 300 to about 500 psig.

The pressure rating of a reactor is of course the maximum pressure at which a particular reactor is designed and constructed to safely operate in accordance with manufacturer's specifications. In established installations, safety engineers may impose lower maximum pressure limits for safe operation, especially in the case of reactors that have been in service for long periods of time, and in this case it is prudent to observe such maximum reduced pressure limits. The point here is that in general the higher the pressure the better the reaction rate, but of course one should not operate at a total pressure that could result in sudden release of pressure via rupture of a safety disc or the like.

Among suitable Lewis acids for use in conducting the carbonylation reaction are such Lewis acids as, for example, $AlCl_3$, $FeCl_3$, $CuCl$, $CuCl_2$, $SnCl_4$, $SbCl_5$, $TiCl_4$, $ZnCl_2$, and corresponding bromide, iodide, or fluoride salts. Mixtures of two or more such Lewis acids can also be used. Lewis acids other than halide salts suitable for use in the practice of this invention include, but are not limited to, tris (pentafluorophenyl)borane and tris(pentachlorophenyl) borane. As noted above, use of Lewis acid chloride salts is generally preferred, with aluminum chloride being the most preferred Lewis acid.

If desired, the carbonylation can be conducted in an inert liquid solvent or diluent such as a saturated aliphatic or cycloaliphatic hydrocarbon.

A preferred way of carrying out this reaction involves the following steps: First, fluorobenzene is mixed with aluminum chloride to form a white to straw-colored slurry in an autoclave. Next, a fixed amount of anhydrous HCl is introduced into the autoclave under pressure, the resulting mixture is heated, and the system pressure is brought up to some desired value via the addition of CO. CO is continuously fed into the system to maintain that pressure throughout the reaction. Alternatively, the CO can be fed semi-continuously whereby the total pressure cycles between selected upper and lower pressures. The rate of uptake of carbon monoxide typically increases rapidly after an induction period, and rapidly decreases at the end of the reaction. Thus the reaction is deemed complete once the CO uptake rate has dropped off significantly from its peak rate. With initial loadings of $AlCl_3$ and fluorobenzene (BzF) of up to at least a 55:45 wt/wt, respectively, the reaction mass at the end of the reaction is composed of a light brown to brown single phase liquid.

It is reasonable to expect that after a reading of this disclosure, those of ordinary skill in the art will envision other suitable ways of conducting the process without departing from the purview of this invention.

A non-limiting, but reasonable, explanation of the process chemistry involved in this reaction is that the hypothetical acid chloride of formic acid, HCOCl, can be thought to form from the reaction of HCl & CO. This species then reacts with aluminum chloride to form a hypothetical $[HCO]^{\oplus}[AlCl_4]^{\ominus}$ ion pair (or more likely a polar, covalent compound, HCO-Cl-$AlCl_3$). $[HCO]^{\oplus}$ is electrophilic and is attacked by the electrons of the fluorobenzene ring to form an $FC_6H_5CHO^{\ominus}$ species which rapidly loses $H^{\oplus}$ to form 4-fluorobenzaldehyde (4FBA). The other "products" in this reaction, $H^{\oplus}$ and $AlCl_4^{\ominus}$, can rapidly rearrange to regenerate HCl & AlCl3. It should be noted that the reaction is deemed catalytic in HCl but not in $AlCl_3$ because the $AlCl_3$ forms a relatively strong complex with the 4FBA that is produced, rendering it largely unavailable for promoting further conversion of BzF to 4FBA at temperatures up to at least 80° C. Based upon the utilizations observed in conducting the process, the complex stoichiometry is about 1 molecule of 4FBA per 1.3–1.5 molecules $AlCl_3$. The heat of reaction is approximately 8–10 kcal/gmol of 4FBA produced.

Four major/important byproducts have been identified: 2-fluorobenzaldehyde (2FBA), 3-fluorobenzaldehyde (3FBA), chlorobis(fluorophenyl)methane (CBFPM), and oligomeric materials. 2FBA and 3FBA are formed as a natural consequence of the formation of 4FBA. The ratio of 2FBA to 3FBA to 4FBA is approximately 1.8:0.2:98.3, and is essentially invariant over a temperature range of 60° C. to 80° C. It is contemplated that use of a bulkier Lewis Acid in place of $AlCl_3$ may improve the split of isomers. CBFPM is presumed to be formed along with HCl from the reaction of 4-fluorobenzal chloride, $FC_6H_4CHCl_2$, with fluorobenzene in the presence of $AlCl_3$. 4-Fluorobenzal chloride in turn is presumed to form from 4FBA via reaction with 2 moles of HCl (water would be the other product). The other byproduct, oligomeric fluorophenyl rings with bridging methylene (—CH2—) and carbonyl (—CO—) groups is thought to form from 4FBA and fluorobenzene.

On the basis of the experimental results obtained to date, the following effects of process variables have been noted:

a) HCl in solution—Using concentrations of HCl between 0.01 kg to 0.03 kg of HCl per kg of $AlCl_3$/fluorobenzene slurry (50:50 wt/wt), for a fixed total system pressure (CO +HCl), increasing the concentration of HCl in solution increases reaction rates up to a point, but at the expense of producing greater amounts of CBFPM. Taken to an extreme, however, where the concentration of dissolved HCl is sufficiently high so that the partial pressure of gaseous HCl in the vapor space equals the system pressure (no CO present), the reaction rate would be expected to be zero. The ratio of 2FBA to 4FBA is invariant to HCl concentration in the solution.

b) Solids loading—At low ratios (40:60 $AlCl_3$:fluorobenzene, wt/wt), $AlCl_3$ utilizations suffer but the selectivities (2FBA:4FBA, CBFPM:4FBA) are unaffected as is reaction time. (Note that throughput will be affected, however, since less 4FBA is produced per batch at the lower loadings). At higher ratios (55:45 $AlCl_3$:fluorobenzene, wt/wt), all utilizations, selectivities, and reaction times are comparable to the ratio typically used (50:50). Going to even higher ratios can be preferable because of the potential for higher throughput, but this needs to be balanced with the potential processing difficulties that could accompany the higher solids loading (ease of stirring the initial aluminum chloride/ fluorobenzene slurry coupled with the possibility that the ending reaction mixture may consist of a liquid phase plus a solid phase rather than a single liquid phase).

c) Temperature—As temperature is increased over the range of 45° C. to 80° C., reaction rates also increase but so does the formation of byproducts other than 2FBA and 3FBA (the ratio of 2FBA to 4FBA is unaffected by temperature from 60–80° C.). Below 45° C., the carbonylation reaction does not proceed at an appreciable rate.

d) Total system pressure—For a fixed ratio of HCl to CO, reaction rates increase with increasing system pressure. Therefore, setting the system pressure to slightly under the pressure rating of the autoclave being used is preferred. If the reaction is conducted at below about 150 psi, it is expected that a CO carrier will increase reaction rates. Of the CO carriers CuCl, $TiCl_4$, and $ZrCl_4$, $TiCl_4$ clearly is preferred because of its high activity.

e) Time between finish of carbonylation reaction and start of aqueous quench—The post-carbonylation reaction mass is stable for 20+ hours at ambient atmospheric temperature and pressure once the HCl and the residual CO have been vented off, and as such, this makes a good stopping point in conducting the process, if use of a stopping point is deemed necessary or desirable. A specific study of the stability of the reaction mixture has not been undertaken (i) before the HCl & CO have been vented off, or (ii) at elevated temperatures. However, since it is likely that CBFPM is produced via reaction of 4FBA with HCl and since oligomers are being formed, storage of the reaction mixture at elevated temperatures or in the presence of HCl is not recommended.

Figure 1:
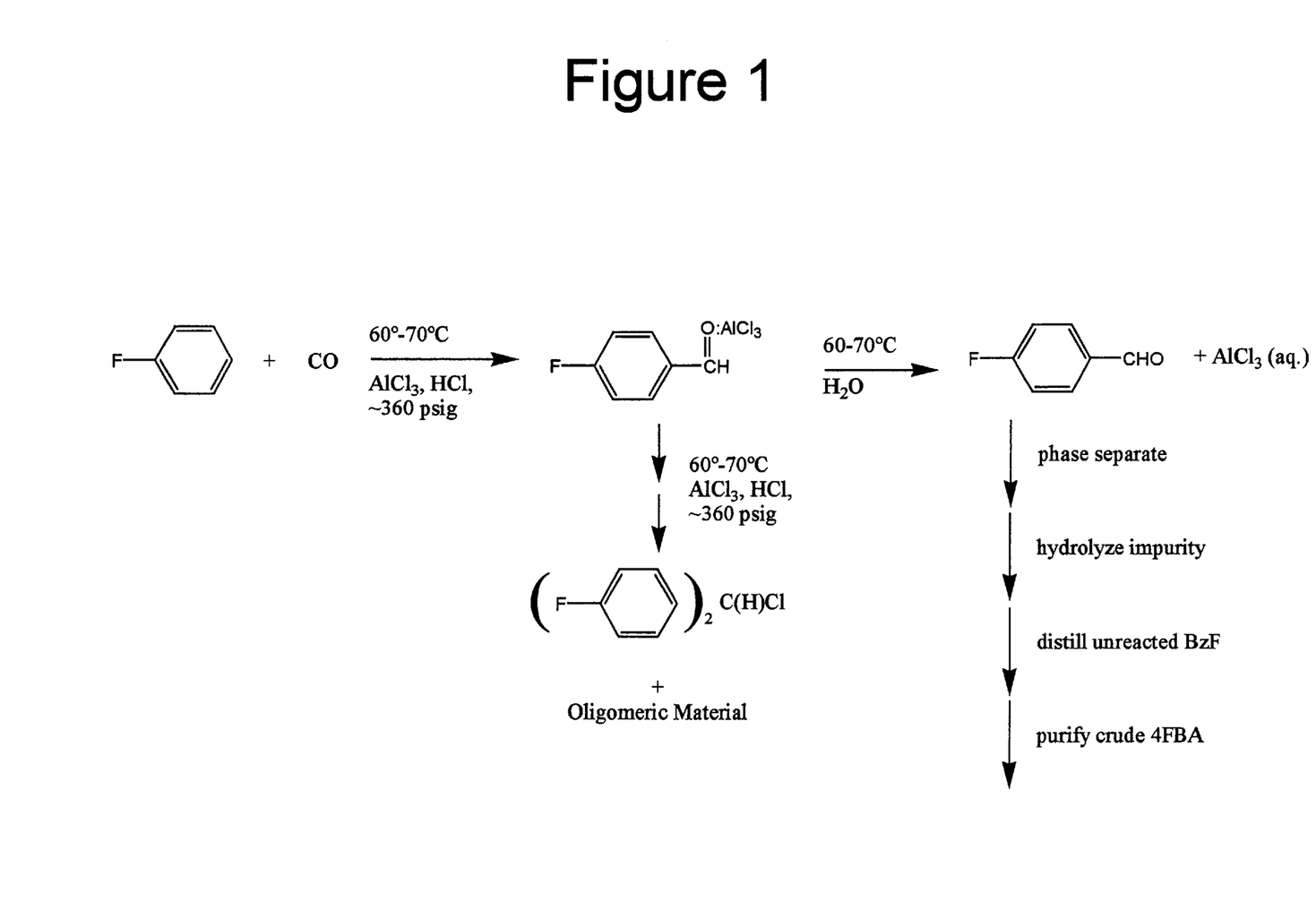
FIG. 1 is an illustration and summary of preferred conditions and preferred steps used in carrying out a process of this invention in a preferred manner.
Figure 2:
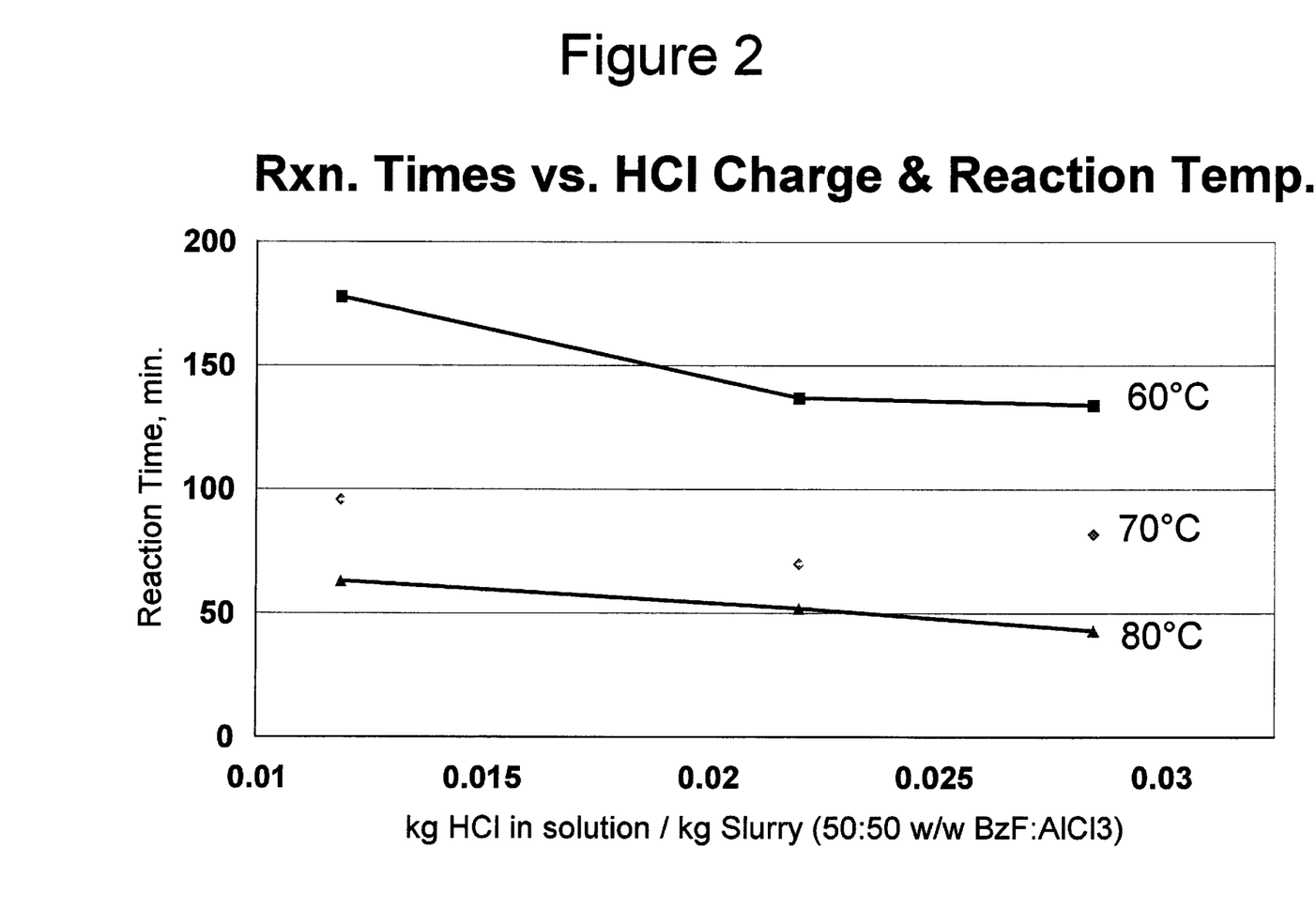
FIG. 2 is a graphical representation of experimental results obtained at a total operating pressure of 380 psig illustrating the effect of temperature and HCl charge on reaction times.
Figure 3:
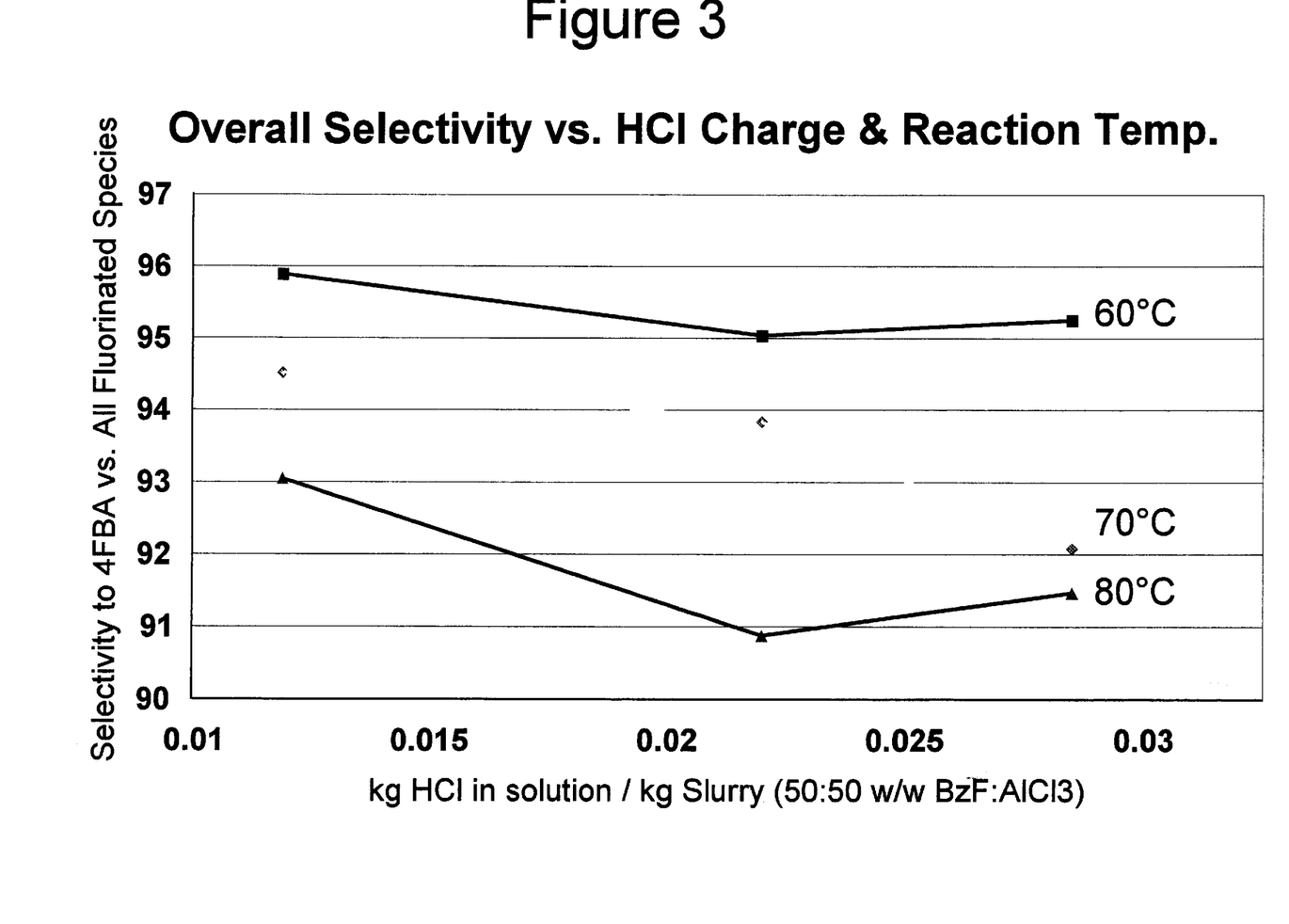
FIG. 3 is a graphical representation of experimental results obtained at a total operating pressure of 380 psig illustrating the effect of temperature and HCl charge on reaction selectivity to 4-fluorobenzaldehyde versus all fluorinated species formed.
Figure 4:
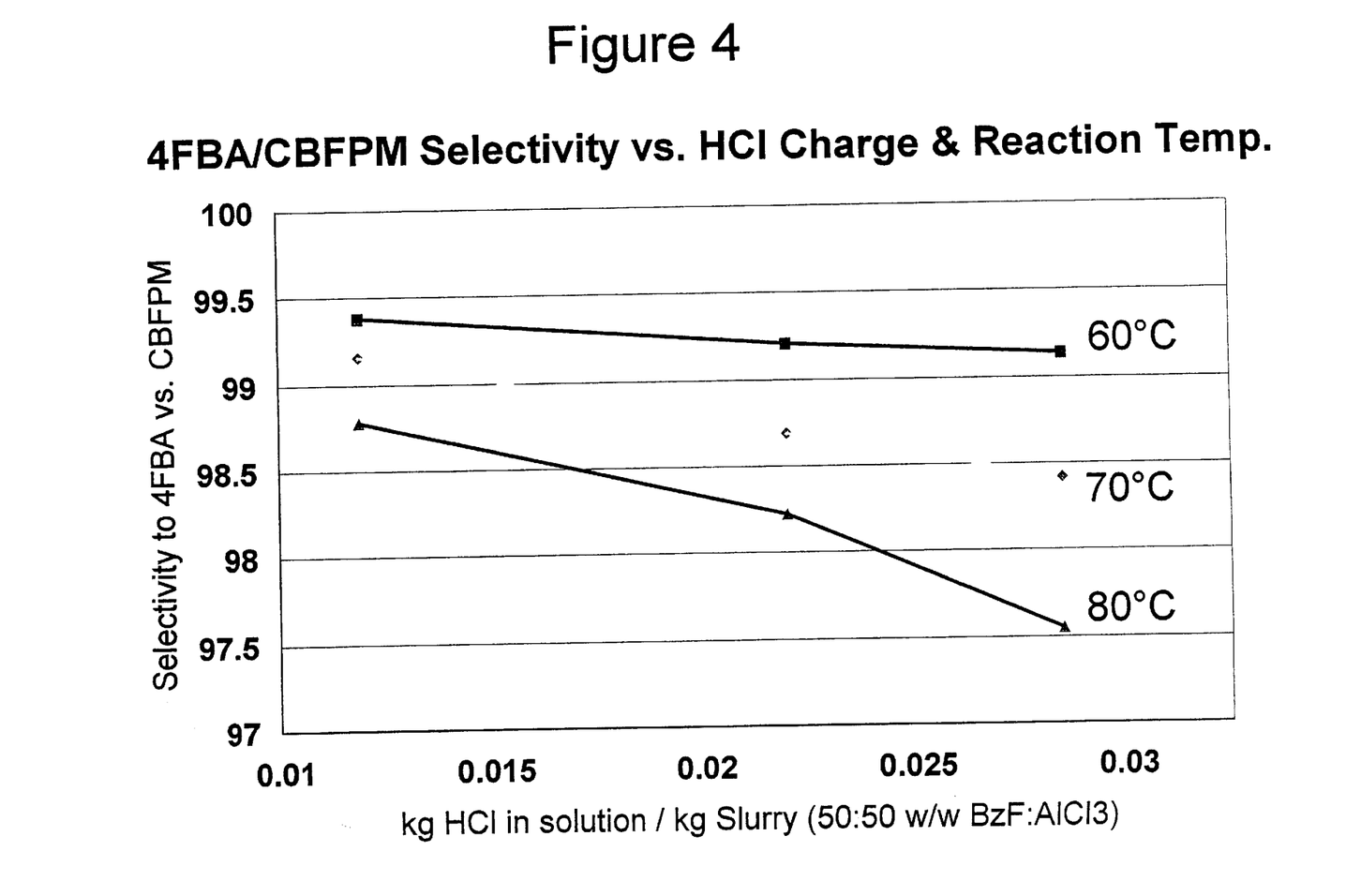
FIG. 4 is a graphical representation of experimental results obtained at a total operating pressure of 380 psig illustrating the effect of temperature and HCl charge on reaction selectivity to 4-fluorobenzaldehyde versus chlorobis(fluorophenyl)methane by-product.
Figure 5:
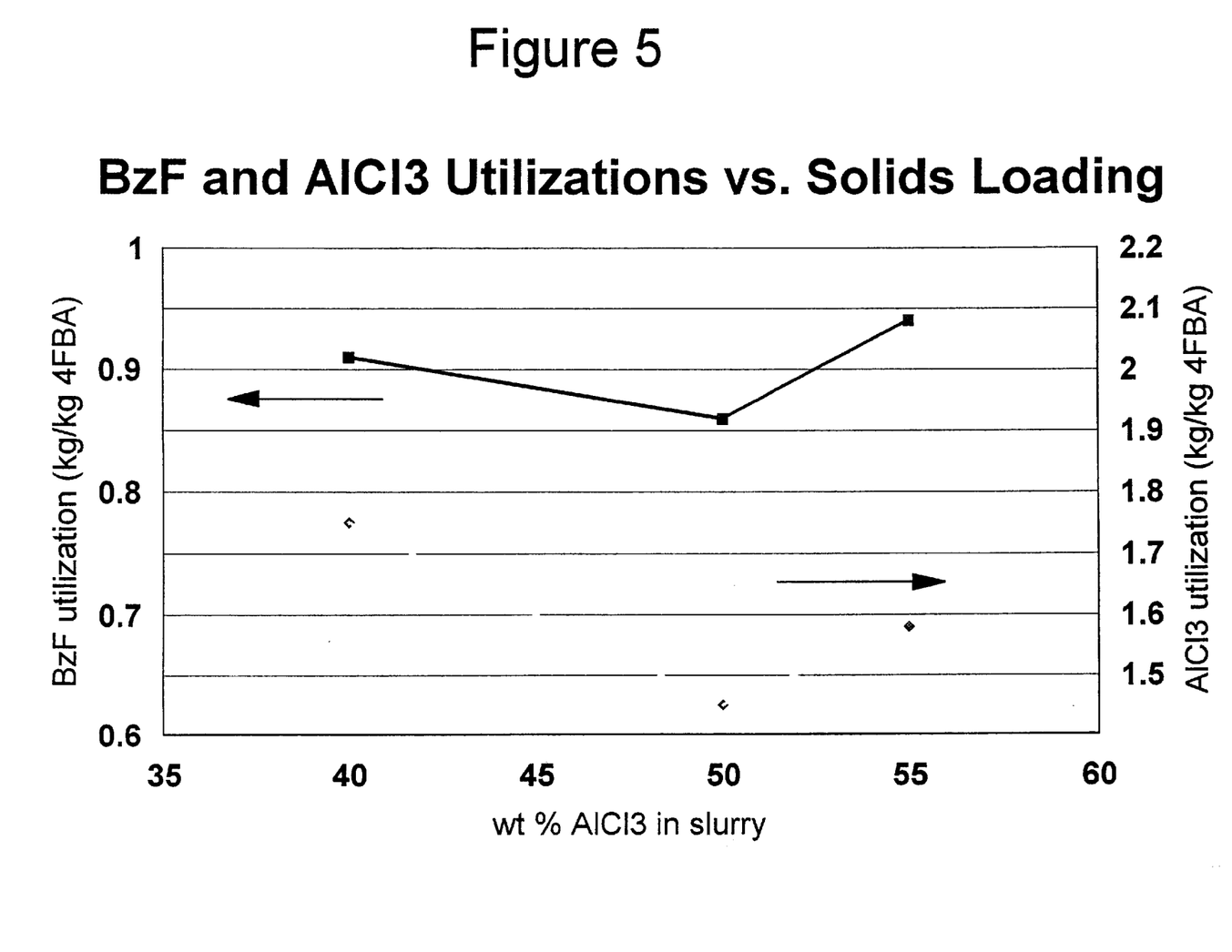
FIG. 5 is a graphical representation of experimental results obtained at a total operating pressure of 380 psig illustrating the effect of solids loading on raw material utilizations.

A number of carbonylation reactions were carried out pursuant to this invention. The general procedure used was as follows: First, fluorobenzene was mixed with aluminum chloride to form a slurry in an autoclave. Next, the autoclave was pressure vented with HCl without agitation to remove nitrogen from the vapor space. Afterwards, a fixed amount of anhydrous HCl was introduced with stirring into the autoclave under pressure, the resulting mixture was heated, and the system pressure was brought up to some desired value via the addition of CO. CO was continuously fed into the system to maintain that pressure throughout the reaction. The reaction was deemed complete once the CO uptake rate had dropped significantly from its peak rate. The particular variables studied and the results of these reactions are presented graphically in FIGS. 2–5. In all cases the total reaction pressure was kept at 380 psig. The results plotted in FIGS. 5 were from runs performed at 60–65° C. It was concluded from FIG. 2 that under the conditions used, higher reaction temperatures increased reaction rates, and that up to a point higher proportions of HCl relative to the 50:50 wt/wt slurry of fluorobenzene to $AlCl_3$ also increased reaction rates. The conclusions from the results shown in FIGS. 3 and 4 were that under the conditions used, higher temperatures had a fairly large negative impact on overall selectivity, that higher HCl charges had a slight negative effect on selectivity, that poorer selectivities at higher HCl loadings and at higher temperatures are apparently due to increased CBPFM formation, and that higher HCl loadings may have less of an effect at lower temperatures on CBPFM formation. From the results plotted in FIG. 5 it was concluded that under the conditions employed, use of a 50 wt % $AlCl_3$ slurry minimizes both $AlCl_3$ and fluorobenzene utilizations.

Quench and Wash Steps

As noted above the carbonylation reaction mass is quenched with water to liberate 4-fluorobenzaldehyde from the aluminum chloride complex and thereafter the 4-fluorobenzaldehyde is separated from chlorobis (fluorophenyl)methane and other by-products. In conducting the quenching step, it is desirable to either feed the carbonylation reaction mass into a body of the water or other suitable quenching liquid, or co-feed a stream of the carbonylation reaction mass and a stream of the water or other suitable quenching liquid into a vessel capable of mixing these streams together, such as a static mixer or a vessel equipped with agitation capabilities. While it is possible to add the water or other suitable quenching liquid to the carbonylation reaction mass, such procedure is less preferred as there is a tendency for solids or gels to form along with the possibility of localized boiling to occur. In preferred embodiments a sequence of a quench step and a wash step is used followed by a workup of the washed reaction mass.

In the quench step, the complex between $AlCl_3$ and 4-fluorobenzaldehyde (4FBA) is broken by quenching the reaction mass with water (containing approximately 1% HCl). The complex between $AlCl_3$ and 4FBA is broken in this separate operation because of the large heat of solvation for $AlCl_3$ being released. More particularly, the heat of solvation is approximately 90 kcal/gmol of $AlCl_3$ being dissolved in the water. Although the water can be added to the reaction mass, or the reaction mass and water can be co-fed into a suitable vessel, the preferred procedure is to add the reaction mass to a suitable quantity of the slightly acidified water. The amount of water used during the quench can be varied as long as there is a sufficient quantity to break all of the complex present and to accommodate the heat of solvation. Preferably the amount of water used is such as to produce an aqueous phase from the quench step containing a predetermined quantity of $AlCl_3$ such as for example a 20, 25 or 30 wt % solution. Operations producing an approximate 27 wt % $AlCl_3$ solution have been found desirable as the solution is of commercial utility. Following the quench, the aqueous phase and the organic phase are separated. Desirably, the organic phase is then washed with 1% HCl to remove trace aluminum salts which could precipitate and act as emulsifying agents downstream. After washing the organic phase with such 1% HCl, the organic phase is cut from the aqueous phase and is then purified. The 1% HCl used in this wash step can then be used as the quench HCl solution in an ensuing batch operation.

Use of water without any acid is also possible when removing the aluminum salts, but can, on occasion, lead to the precipitation of those salts. A third possibility is to use an aqueous solution of a strong base such as sodium hydroxide during the wash step; if enough sodium hydroxide is used relative to residual aluminum salts, it may be possible to keep all of the salts in solution which makes the processing of the material easier.

As regards by-products, except for some slight hydrolysis of chlorobis(fluorophenyl)methane (CBFPM) to di(fluorophenyl)methanol (DFPM) and HCl, no other reactions are known to occur during the quenching and washing steps. It is to be noted that if desired, it is possible to almost completely hydrolyze the CBFPM during the wash assuming that the ratio of wash water to quenched organic is sufficiently high. In this case, it is preferred to separate the phases and then wash the organic phase with dilute aqueous base to neutralize residual acid contained in the organic phase. However such complete hydrolysis described below should not be attempted during the quench step. Combining the quench and hydrolysis steps is not practicable if the concentration of aluminum chloride in the quench water is high (ex., 27 wt. %) because the hydrolysis is actually an equilibrium reaction in acidic solutions and large amounts of chloride present in the quench water would keep the equilibrium shifted towards CBFPM rather than towards DFPM.

One potential way around this may be to combine the quench, wash, and hydrolysis steps into one by quenching into water containing a strong base such as sodium hydrox- ide. The possible precipitation of aluminum salts during such a workup along with the possible degradation of a portion of the reaction mass by the base would need to be weighed against its advantages. Alternately, the wash and hydrolysis steps might be able to be combined either by: (1) washing/hydrolyzing with a sufficiently large ratio of acidic aqueous phase to organic phase to drive the equilibrium between CBFPM and DFPM much in favor of DFPM or (2) washing/hydrolyzing using an aqueous solution of a strong base such as sodium hydroxide where the conversion of CBFPM to DFPM is essentially irreversible (again, the possible degradation of a portion of the reaction mass by the base must be considered). In the case of (1) it is again preferred to separate the phases and wash the organic phase with dilute aqueous base to neutralize residual amounts of acid present in the organic phase. Before trying any of these alternatives, it would be prudent to perform a few preliminary laboratory scale experiments to ascertain the suitability of these workup routes.

On the basis of experimental results obtained to date, the following effects of process variables have been noted:
a) Quench Temperature—Over the range of 45–70° C. no obvious differences in process chemistry have been observed. Based upon the fact that a subsequent hydrolysis of CBFPM step described below has successfully been run at 130° C., quench temperatures up to at least 130° C. should be satisfactory as long as there are no material of construction issues related to use of such higher quench temperatures. At high temperatures, fluorine on 4FBA and/or BzF may possibly be replaced with —OH or —Cl.
b) Wash Temperature—Wash temperatures were conducted at ambient temperatures for convenience purposes. At these temperatures the rate of hydrolysis of CBFPM to DFPM is slow. If conducted at elevated temperatures such as ~80° C. and with a sufficient amount of aqueous to organic, the rate of CBFPM hydrolysis would be expected to become significant.

Except as noted above, the conditions used in the quench and washing steps are not of any particular criticality. For example, the duration of the quenching step can be varied quite extensively. On a laboratory scale quench periods in the order of about 45 minutes at temperatures in the range of about 45 to about 70° C. have proven entirely satisfactory. Similarly the phase cuts can be conducted at various temperatures at which the phases remain as liquids, and typically it is convenient to conduct the phase cuts at about room temperature, e.g., ca. 20–30° C.

Hydrolysis and Workup Steps

In the hydrolysis step, CBFPM is usually hydrolyzed to DFPM and a chloride salt (e.g., NaCl) under basic conditions. The CBFPM is in an organic phase containing at least 4FBA and typically other by-products as well, and the organic phase is mixed with an aqueous phase of a suitable inorganic base whereby the hydrolysis focuses upon the CBFPM. If this hydrolysis is not performed, CBFPM will hydrolyze during a subsequent BzF/H2O strip to yield DFPM and HCl. This is undesirable as the HCl can be corrosive to materials of construction used in common distillation apparatus. It is also important to remove CBFPM for another reason; the final product may discolor upon exposure to light if it contains CBFPM. This is due to photolytic liberation of chlorine which in turn will generate color bodies in situ. The hydrolysis should proceed via an $S_N1$ mechanism:

(FC6H4)2CHCl (aq)→(FC6H4)2CH$^\oplus$+Cl$^\ominus$

In the conduct of this basic hydrolysis step, any residual acid remaining in the organic phase from prior processing will be neutralized.

Because of the high specificity of the carbonylation reaction, the amounts of CBFPM present in the organic phase are quite small. Thus there are no problems associated with the heat of reaction generated in this basic hydrolysis reaction—the heat of reaction for the hydrolysis is deemed inconsequential.

No side reactions have been observed when the hydrolysis reaction is conducted at or below 130° C. when using a 7 wt. % solution of sodium carbonate. This includes: (1) the Cannizzaro reaction which would disproportionate two moles of 4FBA into one mole of 4-fluorobenzoic acid (sodium salt) and one mole of 4-fluorobenzyl alcohol, (2) loss of fluorine from the 4FBA ring to generate inorganic fluoride and 4-hydroxybenzaldehyde, and (3) loss of fluorine from the remaining BzF to form inorganic fluoride and phenol.

It is preferred to use an aqueous solution of sodium carbonate in conducting the alkaline hydrolysis of CBFPM to DFPM. However other inorganic bases can be used, such as lithium carbonate, potassium carbonate, sodium hydroxide, sodium oxide, potassium hydroxide, potassium oxide, sodium bicarbonate, and other similar bases. Concentration of the basic solution is largely discretionary. For example, in the case of aqueous alkali metal carbonate solutions, hydrolysis rates should be invariant to alkali metal carbonate loading as well as to the pH of the aqueous phase be cause of the $S_N1$ mechanism involved. Thus although 7% aqueous solutions of sodium carbonate have been used with considerable success, there is no reason to suppose that other concentrations of this or other inorganic bases will not work satisfactorily, provided of course that the amount of ba se used under any given set of operating conditions does not cause substantial undesirable hydrolysis of other components in the organic phase being treated. Thus in any situation where the suitability of an aqueous base solution for use in conducting this hydrolysis is not known, it would be prudent to perform a few preliminary laboratory scale experiments to ascertain the suitability of the aqueous bas e solution for this use.

On the basis of experimental results obtained to date, the following effects of process variables have been noted:
A) Temperature of hydrolysis—CBFPM hydrolysis rates increase rapidly over the range from 25 to 130° C. Both 4FBA and BzF are stable in 7% aqueous carbonate solution even at 130° C. for periods of at least a few hours.
B) Ratio of aqueous carbonate solution to or organic phase being treated—In hydrolysis with 7% aqueous sodium carbonate solutions, hydrolysis rates decrease with decreasing ratios of the aqueous solution to the organic phase which may be due to the hydrolysis taking place in the aqueous phase rather than in the organic phase.

Typically the hydrolyzed organic phase will be composed of 4-fluorobenzaldehyde, fluorobenzene, 2-fluorobenzaldehyde, di(fluorophenyl)methanol, water, and some other by-product(s).

As an illustration of the effectiveness of using a dilute aqueous alkaline solution for effecting the hydrolysis, a typical reaction mixture containing about 1.3 wt % of chlorobis(fluorophenyl)methane contains essentially no detectable amount of this compound after such hydrolysis. Instead, the treated organic solution contains about 1.2% of di(fluorophenyl)methanol.

The remaining steps in the workup procedure can be varied, depending, for example, on such factors as the type of processing equipment available at plant site, whether the desired product is 4-fluorobenzaldehyde or a mixture of 4-fluorobenzaldehyde and 2-fluorobenzaldehyde, whether the product is to be isolated or subjected to a reaction in situ, and if the product is to be isolated, the purity desired.

In a preferred workup procedure of this invention, where purified 4-fluorobenzaldehyde is the desired product, the following steps are carried out on the hydrolyzed mixture after completing the alkaline hydrolysis:
a) water and fluorobenzene are stripped/distilled from the organic phase;
b) a fraction composed of 2-fluorobenzaldehyde along with some 4-fluorobenzaldehyde is distilled from the residual organic phase from a), 2FBA being more volatile than 4FBA and
c) a fraction of reasonably pure 4-fluorobenzaldehyde is separated by distillation from the heavies remaining in the residual organic phase from b).

Figure 6:
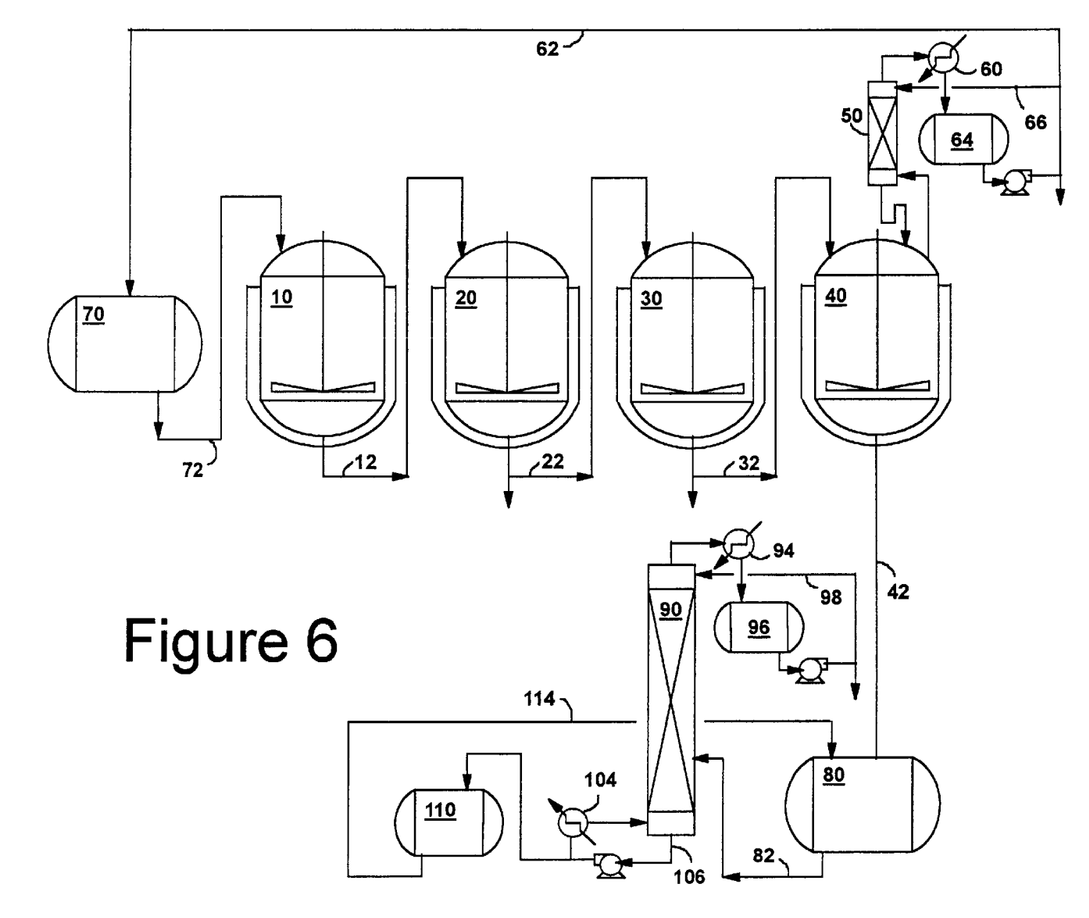
FIG. 6 is a schematic flow sheet illustrating a plant layout suitable for the practice of this invention.

FIG. 6, which is largely self-explanatory, illustrates one non-limiting manner in which a preferred process of this invention can be carried out on an industrial plant scale. In the operation fresh and recycle fluorobenzene can be used, and preferably it is dried using conventional drying technology.

In the system depicted in FIG. 6, a fluorobenzene/aluminum chloride (BzF/AlCl$_3$) slurry is prepared by charging equal weights of fluorobenzene and aluminum chloride into an autoclave 10, preferably fabricated from Hastelloy B, equipped with a mechanical agitator and means for heating or cooling the autoclave. Then reactor 10 is pressure vented with nitrogen to remove oxygen from the system that was introduced when the autoclave was open to the atmosphere.

Carbonylation is conducted in autoclave 10 by heating the reactor contents to a temperature of about 60–70° C., while charging the reactor with a quantity of gaseous hydrogen chloride that results in a dissolved concentration of between 0.01 to 0.03 kg of HCl per kg of the aluminum chloride/fluorobenzene slurry when the temperature of 60–70° C. has been reached. Next the autoclave is pressurized with CO up to the maximum pressure rating of the vessel, and this pressure is maintained throughout the reaction by continuously feeding CO to the reactor. When the CO uptake rate has dropped significantly, the reaction is deemed complete.

After cooling and venting the HCl and residual CO from reactor 10, the reaction mass is pressure transferred via line 12 to quench vessel 20 containing water and a small amount of HCl (e.g., about 1%). Quench vessel 20 is preferably a glass-lined vessel equipped with cooling means to remove the exothermic heat produced during the quench. After the quench, the contents of quench vessel 20 are allowed to settle into two phases and the denser aqueous phase is drawn off and either discarded or stored for subsequent use or sale in other applications. Then fresh water is added to the quench vessel along with a small amount of aqueous HCl to provide an approximately 1% aqueous solution, and the organic phase is washed with this solution to remove residual aluminum salts. The phases are allowed to settle and the denser organic phase is transferred via line 22 into hydrolysis vessel 30 which already contains an aqueous base, preferably, 7% sodium carbonate. The less dense acidic aqueous phase in quench vessel 20 is preferably used as the quench water for the next batch from autoclave 10.

The contents of hydrolysis vessel 30 are heated to about 130° C. to hydrolyze chlorobis(fluorophenyl)methane to di(fluorophenyl)methanol. The sodium carbonate is used to neutralize the HCl that is generated during the hydrolysis. However, if the materials of construction of hydrolysis vessel 30 are resistant to acid attack, water alone or a dilute aqueous acid may be used for the hydrolysis. Since the hydrolysis under acidic conditions involves an equilibrium between the chlorobis(fluorophenyl)methane and di(fluorophenyl)methanol, if water or dilute aqueous acid is used as the hydrolylic agent, a large excess of water or dilute aqueous acid relative to the chlorobis(fluorophenyl)methane should be used to drive the equilibrium in favor of di(fluorophenyl)methanol. If water or dilute aqueous acid is used, it is desirable to separate the phases and wash the organic phase with dilute aqueous base to neutralize residual acid remaining in the organic phase. On the other hand if an aqueous base is used for conducting the hydrolysis, the reaction is essentially irreversible and thus a large excess of the water is not required. After the hydrolysis is complete, the mixture is cooled and then allowed to settle to separate the phases. The denser organic phase is transferred via line 32 to fluorobenzene recovery still 40.

The contents of still 40 are heated and the more volatile fluorobenzene is separated from the less volatile components in the organic phase via column 50 and condenser 60 and are received into rundown tank 64. Both water dissolved in the organic phase and free water in still 40 will come overhead with the fluorobenzene and will accumulate in rundown tank 64. Reflux to column 50 is supplied from rundown tank 64 via line 66. After completion of the fluorobenzene separation, the contents of rundown tank 64 are transferred via line 62 to storage vessel 70 from which the initial supply of fluorobenzene is drawn via line 72. The material remaining in still 40 is transferred to holding tank 80 via line 42.

Note 1: Transferring fluorobenzene from the bottom of storage vessel 70 into carbonylation autoclave 10 is preferred as it minimizes or eliminates the transfer of any free water that has accumulated in storage vessel 70 from the operation of still 40; the less dense water will float on top of the denser fluorobenzene in storage vessel 70. Transferring substantial amounts of water to autoclave 10 is to be avoided since: (1) water can deactivate the aluminum chloride used in the carbonylation step which in turn will decrease the amount of 4-fluorobenzaldehyde produced per batch and (2) the reaction of water with aluminum chloride is both rapid and highly exothermic so the mixing of large amounts of water and aluminum chloride could pose a safety hazard.

Note 2: Overall process efficiency may be increased by producing several batches of crude 4-fluorobenzaldehyde in carbonylation autoclave 10 and then processing that material through quench vessel 20, hydrolysis vessel 30, and still 40 to holding tank 80 as outlined in the preceding paragraphs before proceeding with the continuous distillation outlined below since starting up a continuous distillation column can prove to be time-consuming.

The contents of holding tank 80 are fed via line 82 into continuous distillation column 90 where the more volatile by-products including 2-fluorobenzaldehyde and 3-fluorobenzaldehyde are removed overhead via condenser 94 into rundown tank 96. Reflux to continuous distillation column 90 is supplied from rundown tank 96 via line 98. The less volatile compounds including 4-fluorobenzaldehyde and di(fluorophenyl)methanol leave in the column bottoms via line 106. A portion of the bottoms is recirculated into the column via column reboiler 104 while the remainder is accumulated in holding tank 110 via line 108. Once all of the material in holding tank 80 has been processed, the contents of rundown tank 96 are discarded. The following vessels and/or lines are then cleaned: holding tank 80, continuous distillation column 90, condenser 94, reboiler 104, rundown tank 96, and lines 82, 106, and 98. Then the contents of holding tank 110 are transferred back to holding tank 80.

The contents of holding tank 80 are fed via line 82 into continuous distillation column 90 where the more volatile 4-fluorobenzaldehyde is removed overhead via condenser 94 into rundown tank 96. Reflux to continuous distillation column 90 is supplied from rundown tank 96 via line 98. The less volatile compounds including di(fluorophenyl)methanol leave in the column bottoms via line 106. A portion of the bottoms is recirculated into the column via column reboiler 104 while the remainder is accumulated in holding tank 110 via line 108. Once all of the material in holding tank 80 has been processed, the contents of holding tank 110 are discarded while the 4-fluorobenzaldehyde product contained in rundown tank 96 is packaged for sale.

Reference to two phase systems in this document does not exclude the possibility that in some cases there may be a rag layer formed between an aqueous phase and an organic phase. Formation of any such rag layer does not depart from the scope of this invention, as in essence the system remains for all intents and purposes as a two phase system.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

It will also be understood that terms such as "substantial" and "essentially" denote that chemical operations or treatments ordinarily do not involve absolutes. Thus instead of describing a variable or a result as an absolute, it is far more realistic to describe the variable or result as being in the substantial vicinity of the expressed variable or result. In short, this document should be read with the application of reason and common sense.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process which comprises:
   a) heating in a reactor a mixture of fluorobenzene and a strong Lewis acid with dissolved hydrogen halide and in an atmosphere of carbon monoxide at a temperature in the range of about 45 to about 100° C. and at a total pressure of at least about 150 psig but no higher than the maximum pressure rating of the reactor, to form a reaction mass containing a Lewis acid complex of 4-fluorobenzaldehyde and at least a halobis (fluorophenyl)methane by-product;
   b) breaking the Lewis acid complex by quenching the reaction mass with a Lewis acid-solvating liquid to liberate 4-fluorobenzaldehyde; and
   c) converting halobis(fluorophenyl)methane into di(fluorophenyl)methanol.

2. A process of claim 1 wherein said hydrogen halide is HCl or HBr.

3. A process of claim 1 wherein said hydrogen halide is HCl.

4. A process of any of claims 1, 2, or 3 wherein said Lewis acid as charged into said reactor is a Lewis acid halide salt.

5. A process of claim 4 wherein said Lewis acid halide salt as charged into said reactor is a chloride salt.

6. A process of claim 4 wherein said Lewis acid halide salt as charged into said reactor is aluminum chloride.

7. A process of any of claims 1, 2, or 3 further comprising either (i) recovering 4-fluorobenzaldehyde from the reaction mass from c), or (ii) using the 4-fluorobenzaldehyde as a reactant without isolation.

8. A process of claim 7 wherein said Lewis acid as charged into said reactor is a Lewis acid halide salt.

9. A process of claim 8 wherein said Lewis acid halide salt as charged into said reactor is a chloride salt.

10. A process of claim 8 wherein said Lewis acid halide salt as charged into said reactor is aluminum chloride.

11. A process of any of claims 1, 2, or 3 wherein said atmosphere of carbon monoxide further includes an inert gas.

12. A process of claim 11 of wherein said Lewis acid a s charged into said reactor is a Lewis acid halide salt.

13. A process of claim 12 wherein said Lewis acid halide salt as charged into said reactor is a chloride salt.

14. A process of claim 12 wherein said Lewis acid halide salt as charged into said reactor is aluminum chloride.

15. A process of any of claims 1, 2, or 3 wherein said atmosphere of carbon monoxide further includes an inert gas, and wherein said process further comprises either (i) recovering 4-fluorobenzaldehyde from the reaction mass from c), or (ii) using the 4-fluorobenzaldehyde as a reactant without isolation.

16. A process of claim 15 wherein said Lewis acid as charged into said reactor is a Lewis acid halide salt.

17. A process of claim 16 wherein said Lewis acid halide salt as charged into said reactor is a chloride salt.

18. A process of claim 16 wherein said Lewis acid halide salt as charged into said reactor is aluminum chloride.

19. A process which comprises:
   a) heating in a reactor a slurry of fluorobenzene and aluminum chloride with dissolved anhydrous or essentially anhydrous HCl and in an atmosphere of carbon monoxide with or without at least one inert gas at a temperature in the range of about 45 to about 100° C. and at a total pressure of at least about 150 psig but no higher than the maximum pressure rating of the reactor, to form a reaction mass containing an aluminum chloride complex of 4-fluorobenzaldehyde and at least chlorobis(fluorophenyl)methane by-product;
   b) breaking the aluminum chloride complex by quenching the reaction mass with an aluminum chloride-solvating liquid to liberate 4-fluorobenzaldehyde;
   c) converting chlorobis(fluorophenyl)methane into di(fluorophenyl)methanol; and
   d) either (i) recovering 4-fluorobenzaldehyde from the resultant reaction mass, or (ii) using the 4-fluorobenzaldehyde as a reactant without isolation.

20. A process of claim 19 wherein in d) the 4-fluorobenzaldehyde is recovered from the resultant reaction mass.

21. A process of any of claims 19 or 20 wherein said temperature is in the range of about 45 to about 90° C.

22. A process of any of claims 19 or 20 wherein said total pressure is at least about 250 psig.

23. A process of any of claims 19 or 20 wherein said temperature is in the range of about 60 to about 70° C., and wherein said total pressure is in the range of about 150 to about 500 psig.

24. A process of any of claims 19 or 20 wherein c) is conducted by hydrolyzing said chlorobis(fluorophenyl) methane by-product to di(fluorophenyl)methanol.

25. A process of any of claims 19 or 20 wherein b) is conducted by (i) feeding reaction mass from a) into said aluminum chloride-solvating liquid, or (ii) co-feeding a stream of reaction mass from a) and a stream of said aluminum chloride-solvating liquid into a vessel equipped with mixing capability.

26. A process of any of claims 19 or 20 wherein the $AlCl_3$:fluorobenzene weight ratio in said slurry is in the range of about 40:60 to about 55:45, and wherein the quantity of dissolved anhydrous or essentially anhydrous HCl in the slurry is in the range of about 0.01 to about 0.03 part by weight of HCl per each part by weight of said slurry.

27. A process of claim 26 wherein said temperature is in the range of about 60 to about 70° C., and wherein said total pressure is in the range of about 150 to about 500 psig.

28. A process of claim 20 wherein:

in b), (i) said aluminum chloride-solvating liquid comprises at least water, (ii) said quenching forms a two-phase liquid mixture composed of an aqueous phase and an organic phase comprised of 4-fluorobenzaldehyde together with unreacted fluorobenzene and by-products which include at least chlorobis(fluorophenyl)methane, 2-fluorobenzaldehyde, and 3-fluorobenzaldehyde, said two-phase liquid mixture optionally containing solids comprising hydrated aluminum chloride, and (iii) said organic phase is separated from said aqueous phase and, optionally, is then washed one or more times with another aqueous phase comprised of at least water with each wash being followed by phase separation;

in c), chlorobis(fluorophenyl)methane is converted into di(fluorophenyl)methanol at least by hydrolyzing chlorobis(fluorophenyl)methane by-product in the separated organic phase from b) to di(fluorophenyl) methanol; and in d), 4-fluorobenzaldehyde is recovered from components in the organic phase from c) by distillation.

29. A process of claim 28 wherein after said organic phase is separated from said aqueous phase in b), said organic phase is washed one or more times with said another aqueous phase, said another aqueous phase being water, dilute acid, or dilute strong base.

30. A process of claim 29 wherein said another aqueous phase is dilute hydrochloric, hydrobromic, or sulfuric acid.

31. A process of any of claims 19 or 20 wherein in conducting a), fluorobenzene is mixed with aluminum chloride to form the slurry in the reactor, anhydrous HCl is introduced into the reactor and dissolved into the slurry before, during, and/or after bringing said temperature into said range of about 45 to about 100° C., and the total pressure in the reactor is brought up to and maintained at said total pressure of at least about 150 psig by means of a continuous feed of gaseous CO to the reactor until the reaction has progressed to a desired extent.

32. A process of any of claims 19 or 20 wherein said atmosphere is comprised of carbon monoxide and at least one inert gas.

33. A process of claim 24 wherein the hydrolysis of said chlorobis(fluorophenyl)methane is effected by use of water.

34. A process of claim 24 wherein the hydrolysis of said chlorobis(fluorophenyl)methane is effected by use of dilute aqueous acid.

35. A process of claim 24 wherein the hydrolysis of said chlorobis(fluorophenyl)methane is effected by use of dilute aqueous base.

36. A process of claim 35 wherein said dilute aqueous base is an alkali metal carbonate or bicarbonate.

37. A process which comprises:

a) heating a mixture of fluorobenzene and aluminum chloride in an atmosphere of carbon monoxide and in the presence of dissolved HCl at a temperature in the range of about 45 to about 90° C., and at a total pressure in the range of about 250 psig up to the maximum pressure rating of the reactor being used to form a reaction mass comprising at least an aluminum chloride complex of 4-fluorobenzaldehyde and chlorobis (fluorophenyl)methane by-product;

b) quenching the reaction mass with water or a dilute aqueous acid to liberate 4-fluorobenzaldehyde from the aluminum chloride complex and to form an organic phase and an aqueous phase free of precipitated aluminum salts;

c) separating the organic phase from the aqueous phase and washing the organic phase optionally one or more times;

d) hydrolyzing chlorobis(fluorophenyl)methane in the organic phase into di(fluorophenyl)methanol by reaction with dilute weak base; and e) optionally, recovering 4-fluorobenzaldehyde from the organic phase.

38. A process of claim 37 wherein in b) said reaction mass is quenched with a dilute aqueous acid.

39. A process of claim 38 wherein said dilute aqueous acid is dilute hydrochloric acid.

40. A process of claim 37 wherein said dilute weak base is an alkali metal carbonate or bicarbonate.

41. A process of claim 37 wherein said dilute weak base is sodium carbonate.

42. A process of claim 37 wherein in b) said reaction mass is quenched with a dilute aqueous acid and wherein said dilute weak base is an alkali metal carbonate or bicarbonate.

43. A process of claim 37 wherein in b) said reaction mass is quenched with dilute hydrochloric acid and wherein said dilute weak base is sodium carbonate.

* * * * *

UNITED STATES PATENT AND TRADEMARK OFFICE
CERTIFICATE OF CORRECTION

PATENT NO.    : 6,455,739 B1
DATED         : September 24, 2002
INVENTOR(S)   : Steven G. Karseboom et al.

It is certified that error appears in the above-identified patent and that said Letters Patent is hereby corrected as shown below:

<u>Column 14,</u>
Line 29, reads "..claim 11 of wherein said Lewis acid a s…" and should read
-- …claim 11 wherein said acid as… --

Signed and Sealed this

Fifteenth Day of February, 2005

JON W. DUDAS
*Director of the United States Patent and Trademark Office*